(12) United States Patent
Lonsky et al.

(10) Patent No.: US 12,427,066 B2
(45) Date of Patent: Sep. 30, 2025

(54) EARPIECE AND MANUFACTURING METHOD AND CUSTOMIZATION METHOD OF THE EARPIECE

(71) Applicant: SONOVA AG, Staefa (CH)

(72) Inventors: Julia Lonsky, Zürich (CH); Konstantin Silberzahn, Meilen (CH); Erdal Karamuk, Mannedorf (CH)

(73) Assignee: Sonova AG, Staefa (CH)

( * ) Notice: Subject to any disclaimer, the term of this patent is extended or adjusted under 35 U.S.C. 154(b) by 851 days.

(21) Appl. No.: 17/269,752

(22) PCT Filed: Aug. 20, 2018

(86) PCT No.: PCT/EP2018/072428
§ 371 (c)(1),
(2) Date: Feb. 19, 2021

(87) PCT Pub. No.: WO2020/038547
PCT Pub. Date: Feb. 27, 2020

(65) Prior Publication Data
US 2021/0315740 A1    Oct. 14, 2021

(51) Int. Cl.
*A61F 11/08*     (2006.01)
*B33Y 80/00*     (2015.01)
*H04R 25/00*     (2006.01)

(52) U.S. Cl.
CPC .............. *A61F 11/08* (2013.01); *B33Y 80/00* (2014.12); *H04R 25/656* (2013.01); *A61F 11/085* (2022.01); *A61F 2210/0071* (2013.01); *A61F 2240/004* (2013.01)

(58) Field of Classification Search
CPC ....... H04R 25/656; A61F 11/08; A61F 11/085
See application file for complete search history.

(56) References Cited

U.S. PATENT DOCUMENTS

| | | | | |
|---|---|---|---|---|
| 3,736,929 A * | 6/1973 | Mills | ....... | A61F 11/08 |
| | | | | 128/864 |
| 3,872,559 A * | 3/1975 | Leight | ....... | A61F 11/08 |
| | | | | 128/867 |
| 7,077,825 B1 * | 7/2006 | Stull | ....... | A61F 7/123 |
| | | | | 604/113 |

(Continued)

FOREIGN PATENT DOCUMENTS

| EP | 1874080 | 1/2008 |
|---|---|---|
| JP | 2012075850 | 4/2012 |

(Continued)

OTHER PUBLICATIONS

English translation, Vallittu et al, 2016; A composite.*
International Search Report and Written Opinion received in International Application No. PCT/EP2018/072428.

*Primary Examiner* — Camtu T Nguyen
(74) *Attorney, Agent, or Firm* — ALG Intellectual Property, LLC

(57) ABSTRACT

The disclosure relates to an earpiece configured to be at least partially inserted into an ear and comprising a core comprising a material that during insertion of the earpiece into the ear is deformable above a transition temperature and non-deformable below the transition temperature. The disclosure also relates to a method of manufacturing the earpiece. The disclosure further relates to a method of customizing the earpiece.

18 Claims, 7 Drawing Sheets

(56) References Cited

U.S. PATENT DOCUMENTS

2018/0206788 A1\* 7/2018 Andersen ............. H04R 25/652
2020/0121507 A1\* 4/2020 Magidson ............... A61F 11/08

FOREIGN PATENT DOCUMENTS

| WO | 1993025053 | 12/1993 |
| WO | 2007087633 | 8/2007 |
| WO | 2015131945 | 9/2015 |
| WO | 2018099562 | 6/2018 |
| WO | 2020038547 | 2/2020 |

\* cited by examiner

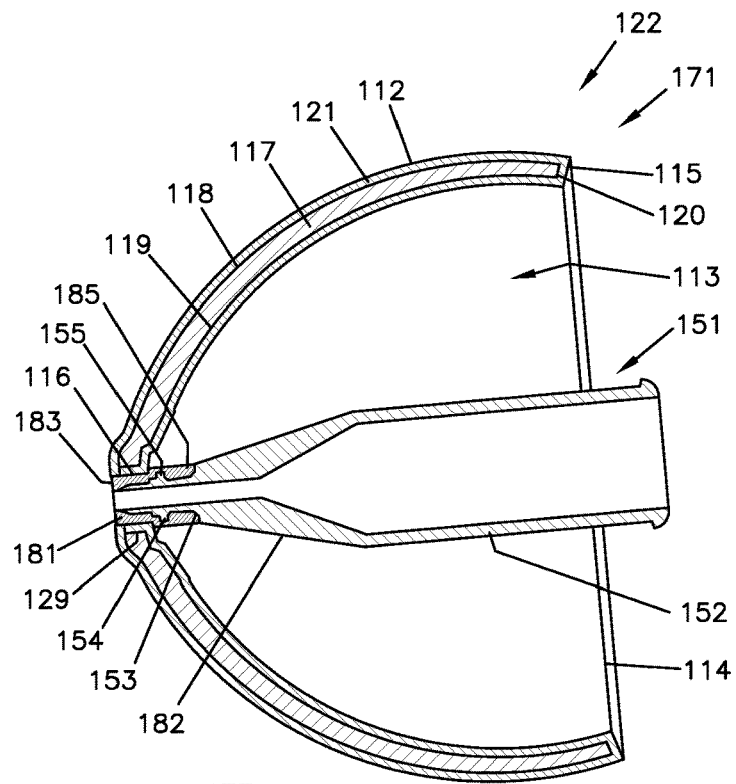

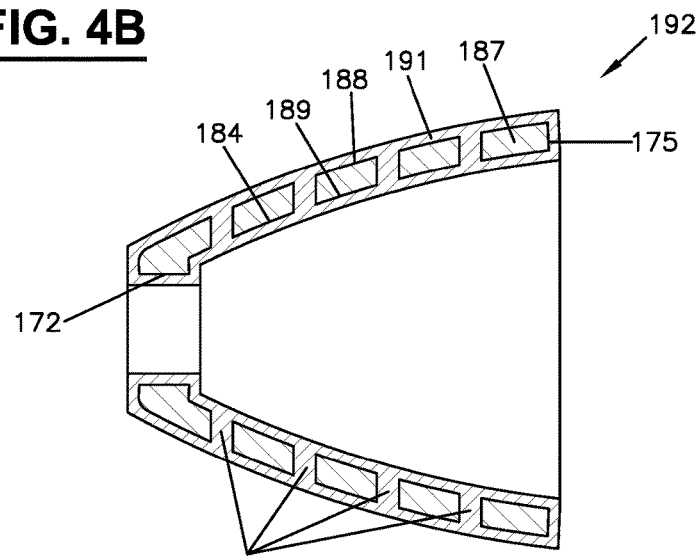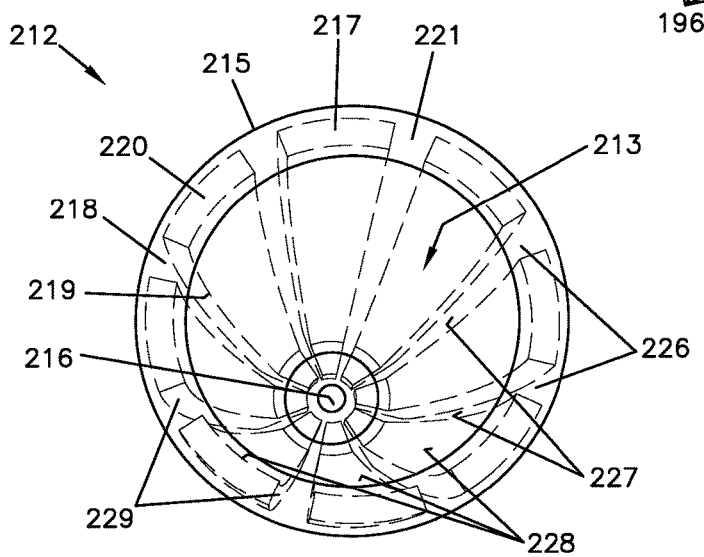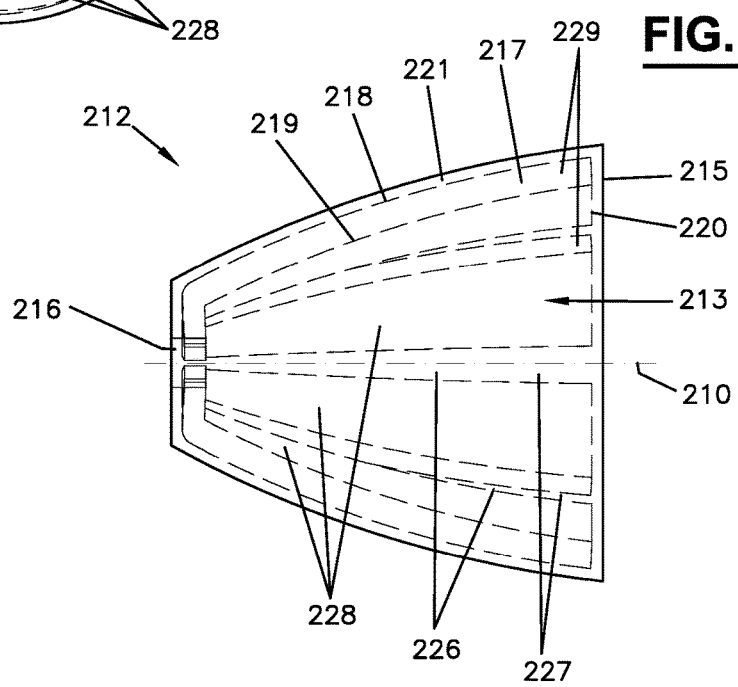

EARPIECE AND MANUFACTURING METHOD AND CUSTOMIZATION METHOD OF THE EARPIECE

TECHNICAL FIELD

This disclosure generally relates to an earpiece, and more specifically to an earpiece that is customizable to an ear shape. The invention also relates to a method of manufacturing the earpiece and a method of customizing the earpiece.

BACKGROUND OF INVENTION

Earpieces can be employed as earplugs offering protection for the ear, for instance against undesired noises and/or against harmful substances entering the ear such as water and/or dirt. Earpieces can also be applied for hearing devices, in particular for positioning at least a component of the hearing device at a region of the ear. Hearing devices may be used to improve the hearing capability or communication capability of a user, for instance by compensating a hearing loss of a hearing-impaired user, in which case the hearing device is commonly referred to as a hearing instrument such as a hearing aid, or hearing prosthesis. A hearing device may also be used to produce a sound in a user's ear canal. Sound may be communicated by a wire or wirelessly to a hearing device, which may reproduce the sound in the user's ear canal. For example, earpieces such as earbuds, earphones or the like may be used to generate sound in a person's ear canal. Furthermore, hearing devices may be employed as hearing protection devices that suppress or at least substantially attenuate loud sounds and noises that could harm or even damage the user's sense of hearing.

Earpieces for hearing devices have long been provided either in an universal size or in a number of sizes from which a user may choose from, or they have been custom-printed in three dimensions or custom-molded and hardened after a curing process. The latter process can account for an improved fit of the earpiece inside the ear and an increased wearing comfort. But this can only be achieved after a rather time-consuming and expensive customization procedure carried out by a health care professional (HCP). First an ear impression needs to be taken from the HCP, from which a customized ear piece is manufactured, requiring a couple of days of work. Then, the user can come back to the HCP to pick-up the customized earpiece. Ideally, it fits at the first go. Otherwise, the earpiece needs to be further adjusted requiring additional time for the customization. Therefore, an on-site customization would be an advantage for the user and for the HPC. On-site customization, however, inherently depends on a material that changes its state of rigidity from very soft where it easily adapts to any required geometry to relatively hard for a permanent fixation of the pre-formed geometry. The material needs to switch between a soft and a hard state very quick and upon a well-defined trigger mechanism.

International patent publication No. WO 2018/099562 A1 to the same applicant discloses a method suitable for such an on-site customization of the earpiece. The method relies on a shape memory material from which the earpiece is formed in a shape of a cavity in which a component of the hearing device is inserted. The method comprises heating the earpiece to evoke a malleable condition at a transition temperature, cooling down the earpiece to a contact temperature intended for contacting the earpiece with the ear, in which contact temperature the malleable condition of the earpiece is preserved, contacting the ear, and attending a hardening time of the shape memory material. Such a method can account for a rather quick and uncomplicated customization of the earpiece.

Nonetheless other solutions may be desirable to offer the user a larger variety of earpieces and corresponding customization processes from which he can chose from. For instance, the user may desire an earpiece that is accustomed to a better mimicking of a specific shape during the customization, which specific shape may still be oriented on the imitation of an individual ear geometry but may also be oriented, even in a more pronounced way, on a prescribed rough basic structure that shall be maintained despite the deformation process on the individual ear. Such a prescribed basic structure may be all the more desirable when a rather complex shape of a preformed earmold shall be maintained during the customization, at least to a specific degree. Moreover, the possibility of a readily available resetting of the earpiece to an original shape, in particular to a shape in which the earpiece had been initially designed, may be an interesting feature, allowing the user to restart the customization from scratch at any time. In addition, a cost factor may play a decisive role for many users when acquiring such an earpiece.

SUMMARY

It is an object of the present disclosure to avoid at least one of the above mentioned disadvantages and to provide an earpiece that can be customized in-situ. It is another object to provide an earpiece that can be customized by the user himself. It is a further object to provide a customizable earpiece as an alternative to other earpieces to broaden the scope of options for a customer. It is another object to provide a customizable earpiece that can revert to an original shape when desired. It is yet another object to equip the customizable earpiece with the capability to also conform to a prescribed shape factor. It is still another object to propose a customizable earpiece that is adequate for rather complex earmold shape factors. It is a further object to provide a customizable earpiece at rather low costs.

At least one of these objects is achieved with an earpiece as described herein and/or in a manufacturing method comprising features described herein and/or in a customization method comprising features described herein.

Accordingly, the disclosure proposes an earpiece, the earpiece configured to be at least partially inserted into an ear. The earpiece comprises a core. The core comprises a material that is deformable during insertion of the earpiece into the ear above a transition temperature and non-deformable during insertion of the earpiece into the ear below the transition temperature. The earpiece comprises a sleeve. The sleeve is at least partially enclosing the core. The sleeve has elastic properties. The elastic properties of the sleeve are selected such that the core conforms to a shape of the sleeve above the transition temperature and the core retains the sleeve in its shape below the transition temperature. Such an earpiece can offer the advantage of allowing an in-situ customization, in particular as a suitable alternative to other available earpieces. The customization may be carried out by the user himself and/or another person such as an HCP. Furthermore, the earpiece may offer the possibility to be adapted to a deformation conforming with a predefined shape factor as defined by the shape of the sleeve. Such a predefined shape factor may be beneficial for achieving any general shaping of the earpiece and particularly when a specific general shape of the earpiece is envisaged to be maintained during customization.

In some implementations, the elastic properties of the sleeve are selected such that the sleeve comprises an original shape and that at least above the transition temperature the sleeve is deformable from the original shape to a deformed shape, in particular during insertion of the earpiece into the ear. In addition, the elastic properties of the sleeve can be selected such that the sleeve is configured to return to its original shape when no force is exerted on the sleeve. In this way, the earpiece may open up a possibility of a resetting of the earpiece to the original shape, as defined by the original shape of the sleeve, when desired by the user after a customization of the earpiece to the ear. In particular, the elastic properties of the sleeve can be selected such that at least above the transition temperature the sleeve bounds the core such that the core conforms to the shape of the sleeve above the transition temperature. In particular, the core can be configured to exert adhesive forces on the sleeve, which adhesive forces can prevent the sleeve to return to its original shape below the transition temperature.

In some implementations, the core has an outer surface, wherein the sleeve is at least partially enclosing the core at its outer surface, in particular such that a contact surface for contacting the ear can be provided by a portion of the sleeve adjoining the core at its outer surface. The outer surface of the core can be adapted to point toward an area of the ear when the earpiece is inserted into the ear. In particular, the elastic properties of the sleeve can be selected such that at least above the transition temperature the sleeve is deformable from the original shape to a deformed shape when the contact surface contacts the ear during insertion of the earpiece into the ear. In particular, the core can be configured to be deformable during insertion of the earpiece into the ear above the transition temperature by the deformation of the sleeve, in particular by the deformation of the sleeve from the original shape to the deformed shape. In some implementations, the core has an inner surface. In particular, the core can be configured to exert adhesive forces at least at one of its inner surface and outer surface, which adhesive forces can prevent the sleeve to return to its original shape below the transition temperature.

In some implementations, the sleeve consists of a single layer provided with the elastic properties. In other implementations, the sleeve comprises a plurality of layers such that the elastic properties are provided by the plurality of layers. For instance, the layers may be formed from the same material and/or different materials. In particular, the layers may be arranged on top of each other, wherein a most inner layer adjoins an outer surface of the core and a most outer layer provides a contact surface for contacting an ear. In some implementations, the core consists of a single material deformable above a transition temperature. In particular, the material may be malleable above the transition temperature. In some implementations, the core comprises different materials deformable above a respective transition temperature. In particular, the materials may be malleable above the respective transition temperature. The transition temperatures of the different materials can be substantially equal corresponding to a single transition temperature of the core. The transition temperatures can also be different from each other, wherein the transition temperature of the core then may correspond to the transition temperature of the material having the highest transition temperature. In some implementations, the transition temperature may also be defined as a transition temperature range ranging from the transition temperature of the material of the core having the lowest transition temperature to the transition temperature of the material of the core having the highest transition temperature. The core can be deformable during insertion of the earpiece into the ear above the transition temperature range and non-deformable during insertion of the earpiece into the ear below the transition temperature range.

In some implementations, the core has an inner surface. The inner surface may surround a receiving space configured for receiving a component of a hearing device. The sleeve may at least partially enclose the core at its inner surface, in particular such that the receiving space is delimited by a portion of the sleeve adjoining the core at the inner surface. In this way, the earpiece can be customized with regard to specific requirements of a positioning of hearing devices in the ear. In some implementations, the receiving space forms a bore at an end of the earpiece. The bore may be configured to be connected to the component of the hearing device. In particular, the component may be a receiver and/or a sound tube of the hearing device. The bore may be provided with a connector for the component. The connector can be configured to connect the earpiece with the component. The connector may be inserted in the bore, in particular such that a part of the connector protrudes into the receiving space. The protruding part may be a flange, by which the component of the hearing device can be received.

The connector may comprise a side wall surrounding a tubular cavity. In some implementations, an outer surface of the side wall is configured to receive the component of the hearing device, the outer surface pointing away from the tubular cavity, in particular such that the component can be plugged and/or screwed onto the outer surface. In some implementations, an inner surface of the side wall is configured to receive the component of the hearing device, the inner surface delimiting the tubular cavity, in particular such that the component can be plugged and/or screwed onto the inner surface. The tubular cavity may be configured to provide for a propagation of sound waves from the component toward the ear canal, when the ear piece is inserted in the ear. The side wall may comprise a circumferential recess in which at least one of the core and the sleeve is arranged. Thus, a reliable mounting of the connector to the core and/or sleeve may be provided. In some implementations, the connector comprises a material different from a material or materials from which at least one of the core and the sleeve is formed. In particular, the connector can be formed from a different material than the core and the sleeve. In some other implementations, the connector comprises a material corresponding to a material of the sleeve. In particular, the core can be formed from the same material than the sleeve. In this way, the elastic properties of the sleeve may also be exploited for the connector. In some implementations, the core has an intermediate surface joining the outer surface and the inner surface. The sleeve may adjoin the intermediate surface.

In some implementations, the transition temperature is selected to be below 90° Celsius. Such a selection of the transition temperature can account for a rather simple and quick provision of the deformable, in particular malleable, condition of the core, wherein the earpiece may be still within an acceptable temperature range to be inserted into a human ear. In some implementations, the transition temperature is selected to be above 50° Celsius. Thus, an undesired or accidental provision of the deformable condition of the core can be avoided by choosing the transition temperature well beyond usually according ambient temperatures. In some implementations, the original shape of the sleeve comprises a shape of at least one of an open-ended sleeve, a dome, and a preformed earmold.

In some implementations, the core comprises a recess on its outer surface. The sleeve may comprise a protrusion extending into the recess. In this way, a retention of the core in its deformable condition above the transition temperature may be enhanced inside the sleeve. The recess may be provided as a through hole. The through hole may extend from the outer surface to the inner surface of the core. Thus, the core retention may be further enhanced in the sleeve above the transition temperature. Beyond that, the adhesion of the sleeve to the core may be increased below the transition temperature. In some implementations, the core comprises a plurality of core sections extending in an axial direction of the receiving space. The core sections may have a gap between each other, in particular in a circumferential direction of the inner surface of the core which is surrounding the receiving space. The sleeve may be provided inside the gap. In particular, the sleeve may comprise a corresponding pultrusion extending into the gap and/or traversing the gap. This may also allow an improved retention of the core and/or an improved adhesion of the sleeve, in particular with respect to an axial direction of the earpiece. The axial direction may be particularly chosen in this respect to be provided with enhanced retention properties, when the axial direction may correspond to an insertion direction of the earpiece inside the ear canal. In addition, a flexibility of the earpiece in the axial direction may thus be improved by exploiting the flexible properties of the sleeve, which may contribute to an easier insertion of the earpiece and an improved wearing comfort.

In some implementations, a stiffening member is provided in the earpiece. The stiffening member may adjoin the sleeve, in particular an inner surface and/or outer surface of the sleeve. The stiffening member may be configured to bias against forces exerted on the earpiece upon insertion of the earpiece into the ear. In this way, an improved stability of the sleeve may be provided when inserted into the ear, in particular such that specific regions of the sleeve, which may be crucial for a general shape to be achieved during the customization, are stabilized. The stiffening member may be configured to provide a larger rigidity than the sleeve. In some implementations, the stiffening member is formed from the same material than the sleeve. In some implementations, the stiffening member is formed from a different material as the sleeve, in particular a material having a larger rigidity.

In some implementations, the sleeve has a hardness parameter in a range in the order of 20 Shore A to 90 Shore A. The sleeve may form a wall having a thickness in a range of at least 0.1 mm. The sleeve may form a wall having a thickness in a range of at most 3.5 mm. In this way, said elastic properties can be advantageously adapted to the mechanical requirements of the earpiece. The sleeve can comprise a material selected from a class which includes silicone, in particular fluoro-silicone, for instance a silicone rubber and/or a fluoro-silicone rubber, an elastomer, in particular a thermoplastic elastomer (TPE), polyurethane (PU), in particular thermoplastic polyurethane (TPU), and compositions thereof.

In some implementations, the core comprises a thermoplastic polymer. In particular, the core may be formed from the thermoplastic polymer. In particular, a thermoplastic polymer exhibiting a desired transition temperature may be selected. The thermoplastic polymer may be selected from a class which includes polycaprolactone (PCL), poly(1,4-butylene adipate) (PBA), polyethylene (PB), ethylene-vinylacetate-copolymer (EVA), polylactide (PLA), and compositions thereof. Such a material may undergo an unlimited number of cycles below and above the transition temperature. In particular, the material may change into a viscos state once crossing the transition temperature, in particular melting temperature. The material may be in a soft condition above the transition temperature, in which it may be configured to be shaped as required. The material may be in a hard condition below the transition temperature, in which it may be configured to stay in this shape. In some implementations, the core is formed from a shape memory material. In particular, the core may be configured to comprise an original shape of the shape memory material substantially corresponding to a shape in which the sleeve in its original shape would also deform the core above the transition temperature, in particular when no external forces are exerted on the sleeve. Thus, the core may be configured to return to an original shape corresponding to the original shape of the sleeve above the transition temperature independent from any forces exerted by the sleeve on the core above the transition temperature., in particular when no external forces are exerted on the sleeve. In some other implementations, the core is not formed from a shape memory material. In particular, the core may be formed from a less expensive material as compared to a shape memory material. In this way, a capability of the sleeve due to said elastic properties to deform the core back to an original shape above the transition temperature, the original shape of the core corresponding to an original shape of the sleeve, when no forces are exerted on the sleeve may be exploited to provide a rather cost-effective earpiece having similar properties than an earpiece comprising a more expensive shape memory material.

A method of manufacturing an earpiece can comprise providing the core and providing the sleeve on the core. The sleeve may be provided on the core such that the sleeve at least partially encloses the core. In particular, the sleeve may be provided on the core such that the sleeve adjoins at least one of an outer surface and an inner surface of the core. In some implementations, the core may be provided by injection molding. In some implementations, the core may be provided by three dimensional printing, in particular a two component three dimensional printing. In some implementations, the core may be provided by filling a hollow sleeve, in particular with a molten thermoplastic polymer. The core may be provided on a connector, in particular molded onto the connector, in particular by a two component injection molding. The sleeve may be provided on the core by at least one of injection molding, in particular two component and/or three component injection molding, three dimensional printing, in particular a two component and/or three component three dimensional printing, compression molding, dipping, manual coating, and spraying the sleeve onto the core.

A method of customizing an earpiece to an ear of a user may comprise heating the earpiece above the transition temperature of the core such that the core is provided in a deformable condition. The method may further comprise inserting the earpiece at least partially into the ear, in particular such that the sleeve is contacting the ear, more particularly such that a contact surface of the sleeve is contacting the ear. In this way, the sleeve may be deformed by the ear, in particular the contact surface may be deformed by the ear. The method may further comprise cooling the earpiece below the transition temperature, in particular inside the ear. The cooling may be executed by simply waiting a sufficiently long time in which a temperature of the earpiece adjusts to the temperature of the ambient environment. In this way, the core may be provided in a non-deformable condition. The sleeve may be retained in its shape by the core. In particular, the sleeve my by attached to the core by adhesive forces of the core. The adhesive forces may be provided on at least one of an outer surface and an inner surface of the core.

In some implementations, the sleeve may have at least one of the following properties:
- the sleeve may be vulcanized, in particular such that the sleeve has no melting temperature or a substantially higher melting temperature than the core;
- the sleeve may be configured to provide an over-all pre-shape, in particular above the transition temperature of the core, for instance such that a dome may stays a dome even when deformed;
- the sleeve may not agglomerate or tear during forming, for instance such that an earpiece to be applied on a concha remains in an over-all concha shape and may not change its shape to the shape of a dumpling;
- the sleeve may allow for a memory-effect when heated without an outer force.
- the sleeve may exert a force which will move a heated, in particular fluidic, core back or close to its original shape, for instance such as a shape memory polymer, in particular to a shape in which it was produced;
- the sleeve may shield the inner core against unfavorable chemical environments, for instance when using a fluorinated sleeve, in particular a fluoro-silicone rubber, as a material or constituent of a material of the sleeve;
- the sleeve may incorporate a connector and/or other mechanical connections, such as interfaces to head-phones or receiver-in-the-canal (RIC) hearing devices, which may not undergo any mechanical change, in particular above the transition temperature;
- the sleeve may be formed from a soft material, which can allow a mechanical deformation and/or absorb a mechanical deformation in between a connector and the core, in particular a deformed inner core;
- the sleeve may comprise a stiffening member and/or additional mechanical features, such as ribs, to increase its mechanical stability in certain directions during a deformation above the transition temperature, for instance an axial stability for a dome-shaped earpiece;
- the sleeve may be formed of a foam and/or comprise a foam to improve modulus differences, in particular between an ear canal and the earpiece, such that a wearing comfort may be improved; and
- the sleeve may be formed of an insulating material and/or comprise an insulating material and/or incorporate features to reduce a heat transfer relative to an ambient environment, which heat transfer may result for instance in a long-term viscous condition of the core and thus a deformable condition of the core for an undesired long time period.

In some implementations, the core may have at least one of the following properties:
- the core may comprise a transition temperature over which it may melt and/or changes into a viscous condition and below which it may change into a hardened condition;
- said hardened condition below the transition temperature may also comprise a comparatively soft condition, which still has an enhanced hardness as compared to the condition above the transition temperature;
- said melting and hardening may be repeatable;
- the transition temperature, in particular melting temperature, may be below that of the sleeve, in particular such that when the core is heated it may be forced back into the original shape of the sleeve;
- below the transition temperature, in particular when the core is in said hardened condition, the core may comprise a significant higher Young's modulus than the sleeve, in particular such that the shape of the core determines the overall shape of the earpiece below the transition temperature; and
- the core may change into a fluidic condition above the transition temperature, in particular when heated up, for instance in a range between 60° Celsius and 80° Celsius, in particular such that the core can then adapt to a geometry imposed by an outer force, for instance an outer force occurring during insertion of the earpiece into an ear.

In some implementations, the core may comprise or consist of a stimuli-responsive polymer. Such a stimuli-responsive polymer may be configured to respond to a defined trigger and to change its mechanical properties upon said defined trigger. An earpiece comprising such a core with a stimuli-responsive polymer may have at least one of the following properties:
- the sleeve may shield the core against unfavorable chemical environments, for instance by forming the sleeve from a material comprising a fluoro-silicone rubber;
- the sleeve may be formed from a different material allowing to incorporate a connector and/or mechanical connections into the sleeve, for instance an interface to head-phones or RICs, such that the material of the sleeve does not not undergo any mechanical change, for instance such that the sleeve does not to induce any leakage when deformed;
- the sleeve may provide an optical barrier and/or a barrier against ultraviolet (UV) radiation; and
- the sleeve may be configured for a colorization and/or a serialization.

BRIEF DESCRIPTION OF THE DRAWINGS

Reference will now be made in detail to embodiments, examples of which are illustrated in the accompanying drawings. In the drawings:

FIG. 3E illustrates a longitudinal-sectional view of an earpiece receiving a component of a hearing device, in accordance with some embodiments of the present disclosure;

FIG. 3F illustrates a perspective sectional view of a core that can be provided in an earpiece, in accordance with some embodiments of the present disclosure;

FIG. 4A illustrates a perspective sectional view of a core that can be provided in an earpiece, in accordance with some embodiments of the present disclosure;

FIG. 4B illustrates a longitudinal sectional view of a wall comprising the core illustrated in FIG. 4A which can be provided in an earpiece, in accordance with some embodiments of the present disclosure;

FIGS. 5A, B illustrate a wall from a top view and a lateral view which can be provided in an earpiece, wherein internal parts are indicated by dashed lines, in accordance with some embodiments of the present disclosure;

DETAILED DESCRIPTION OF THE DRAWINGS

In the following detailed description, numerous specific details are set forth in order to provide a thorough understanding of the subject matter herein. However, it will be apparent to one of ordinary skill in the art that the subject matter may be practiced without these specific details. In other instances, well known methods, procedures, techniques, components, and systems have not been described in detail so as not to unnecessarily obscure features of the embodiments. In the following description, it should be understood that features of one embodiment may be used in combination with features from another embodiment where the features of the different embodiment are not incompatible. The ensuing description provides some embodiment(s) of the invention, and is not intended to limit the scope, applicability or configuration of the invention or inventions. Various changes may be made in the function and arrangement of elements without departing from the scope of the invention as set forth herein.

Figure 1A:
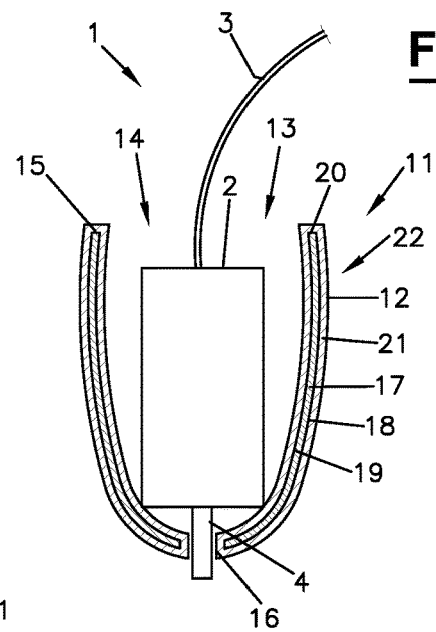
FIGS. 1A-C schematically illustrate a hearing device received by an earpiece that is customized to an ear of a user, in accordance with some embodiments of the present disclosure.

FIG. 1A illustrates a hearing device 1 received by an earpiece 11 in accordance with some embodiments of the present disclosure. Earpiece 11 is provided by a curved wall 12. The curvature of wall 12 is chosen such that a cavity 13 is enclosed by wall 12. Hearing device 1 comprises a housing 2 arranged inside cavity 13. Thus, cavity 13 constitutes a receiving space for hearing device 1. Receiving space 13 comprises an open end 14 delimited by a free end 15 of wall 12. The open end defines an opening 14 through which hearing device 1 is insertable into receiving space 13 and removable from receiving space 13. A cable 3 is connected to hearing device 1. Cable 3 extends from a rear end of housing 2 through opening 14 of receiving space 13 toward an ambient environment of earpiece 11. Earpiece 11 comprises a bore 16 provided as a through hole in curved wall 12. Bore 16 is formed at a second open end of receiving space 13 opposed to first open end 14. The first open end of receiving space 13 forming opening 14 corresponds to a first end of earpiece 11. The second open end of receiving space 13 forming bore 16 corresponds to a second end of earpiece 11. Hearing device 1 further comprises a sound tube 4. Sound tube 4 is inserted in bore 16 such that sound tube 4 extends from a front end of housing 2 through bore 16. In this way, sound waves can be transmitted from a receiver inside housing 2 via sound tube 4 through bore 16 toward an ear drum of a user when earpiece 11 is inserted into an ear of the user.

Earpiece 11 comprises a core 17 and a sleeve 21 forming wall 12. Sleeve 21 encloses core 17, in particular such that a portion of sleeve 21 adjoins an outer surface 18 and an inner surface 19 of core 17. Sleeve 21 provides an enveloping layer of wall 12 such that an outer shape 21 of earpiece 11, as observed from an ambient environment of earpiece 11, substantially corresponds to a shape of sleeve 21. Shape 21, as depicted in FIG. 1A, corresponds to an original shape of sleeve 21. Original shape 21 of sleeve 21 is defined as a state to which sleeve 21 returns due to its elastic properties when no force is exerted on the sleeve. Inner surface 19 of core 17 surrounds receiving space 13. A portion of sleeve 21 adjoining inner surface 19 of core 17 delimits receiving space 13. Outer surface 18 of core 17 points toward an ambient environment of earpiece 11. Core 17 comprises a rear face 20 pointing toward free end 15 of wall 12. Rear face 20 constitutes an inter-face, more particularly an intermediate surface, joining outer surface 18 and inner surface 19. Sleeve 21 adjoins rear face 20 such that free end 15 of wall 12 is constituted by a portion of sleeve 21. Sleeve 21 further adjoins core 17 around bore 16 in wall 12. In this way, sleeve 21 may fully enclose core 17. Core 17 is formed from a material comprising a transition temperature. Below the transition temperature, the material of core 17 is substantially non-deformable, in particular such that core 17 is not malleable below the transition temperature. Above the transition temperature, the material of core 17 is deformable, in particular such that core 17 is malleable above the transition temperature. Core 17 may comprise at least one thermoplastic material, in particular a thermoplastic polymer.

Figure 1B:
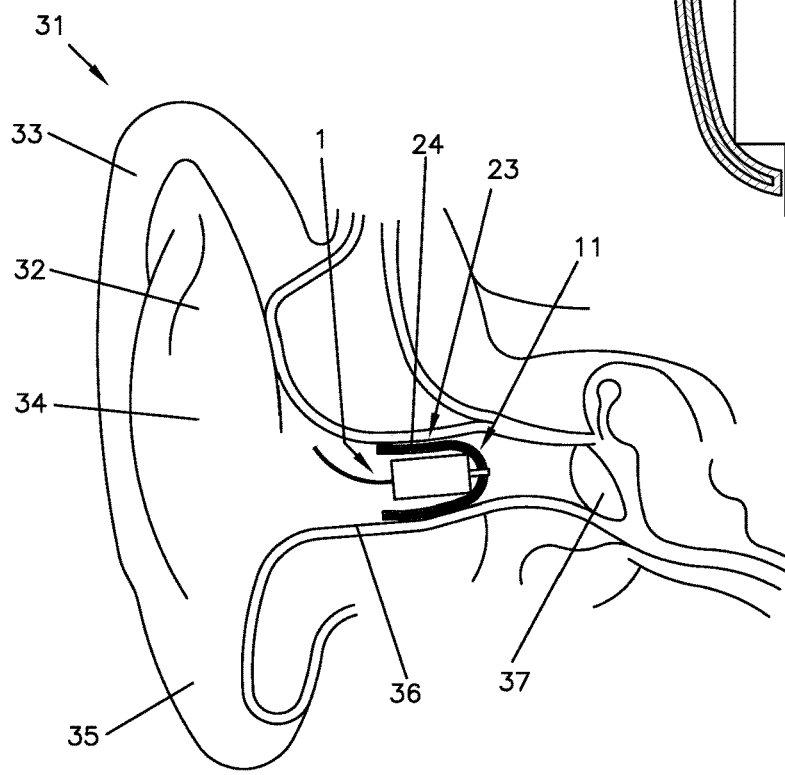

FIG. 1B illustrates an ear 31 of a user to which earpiece 11 shall be customized. Ear 31 comprises an auricle 32 including a helix 33, a concha 34, and an earlobe 35. Ear 31 further comprises an ear canal 36 extending from auricle 32 to an eardrum 37. Earpiece 11 is inserted into ear 31, more particularly from concha 34 into ear canal 36. During insertion, earpiece 11 is configured to conform to an individual shape of ear canal 36 due to the elastic properties of sleeve 21 and the malleability of core 17 above the transition temperature. More precisely, sleeve 21 is deformable from its original shape 22 to a deformed shape 23 when sleeve 21 contacts ear canal 36 upon insertion. A contact surface 24 for contacting ear 31 is provided by a portion of sleeve 21 adjoining core 17 at outer surface 18. Moreover, sleeve 21 constitutes a boundary wall for core 17 contained inside sleeve 21. Thus, sleeve 21 bounds core 17 in its deformable condition such that core 17 conforms to shape 23 of sleeve 21 above the transition temperature. In this way, earpiece 11 can be customized to the individual shape of ear canal 36.

Figure 1C:
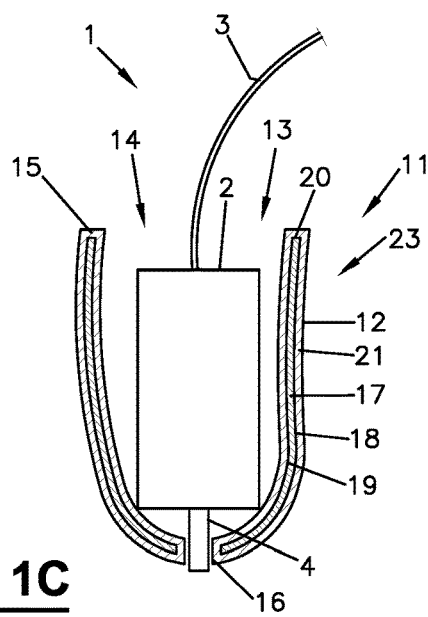

FIG. 1C illustrates earpiece 11 after removal from ear 31, wherein core 17 has been cooled down below the transition temperature before the removal. Earpiece 11 has been retained in deformed shape 23 of sleeve 21. Core 17 exerts adhesive forces at its inner surface 17 and outer surface 18 to sleeve 21 below the transition temperature. The adhesive forces prevent sleeve 21 to return to its original shape 23. In this way, earpiece 11 is customized to the user's ear 31. When core 17 is heated up again above the transition temperature, earpiece 11 returns to original shape 22 of sleeve 21, wherein the deformable condition of core 17 is exploited. In the deformable condition, in particular malleable condition, of core 17, the elastic properties of sleeve 21 are suited to exert a deforming force on core 17 such that sleeve 21 returns to the original shape by deforming core 17. It is noted that core 17 may also exert adhesive forces at its inner surface 17 and outer surface 18 to sleeve 21 above the transition temperature, i.e. when core 17 is in its deformable condition. But intermolecular forces in the material of core 17, such as cohesive forces in between molecules of core 17, may be too weak in the deformable condition of core 17 to counteract a restorative force in sleeve 21 caused by its elastic properties. Thus, sleeve 21 can return to its original shape by deforming core 17. In a non-deformable condition of core 17 below the transition temperature, however, those intermolecular forces and/or cohesive forces in the material of core 17 may be too strong to be overcome by the restorative elastic force of sleeve 21. Thus, deformed shape 23 of sleeve 21 can be conserved below the transition temperature.

Figure 2:
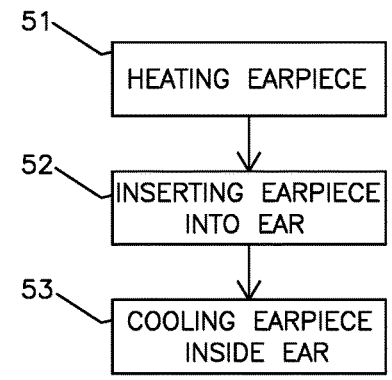
FIG. 2 illustrates a method of customizing an earpiece in an ear of a user, in accordance with some embodiments of the present disclosure.

FIG. 2 illustrates a method of customizing earpiece 11 to ear 31. At 51, the earpiece is heated above the transition temperature of the core. In this way, the core can be provided in a deformable condition, in particular in a malleable condition. At 52, the earpiece is inserted at least partially into the ear. Thus, the sleeve is contacting the ear at its contact surface and deformed by the ear. At 53, the earpiece 11 is cooled down below the transition temperature of the core inside the ear. The cooling down may be executed by waiting a sufficiently long time in which the earpiece adjusts its temperature to a room temperature of the ambient environment. After 53, the earpiece may be removed from the ear by retaining its deformed shape. The earpiece is then customized to an individual shape of the ear. Afterwards, the user may decide to revert the earpiece to the original shape of the sleeve by heating the core up again above the transition temperature.

Figure 3A:
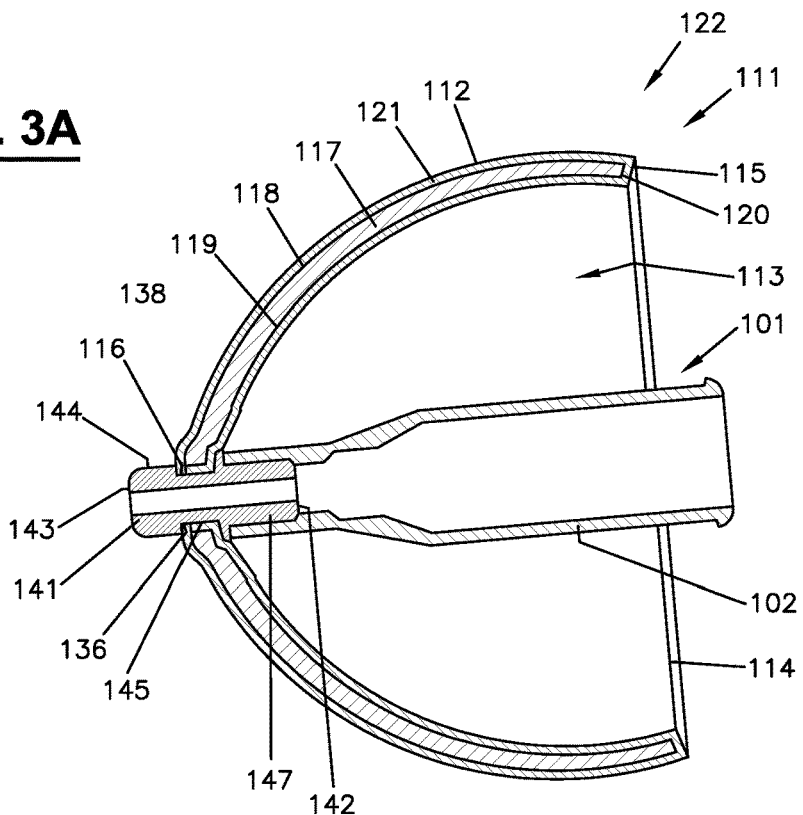
FIGS. 3A-C illustrate a longitudinal-sectional view of an earpiece receiving a component of a hearing device, wherein the earpiece is customized in an individual ear, in accordance with some embodiments of the present disclosure.

FIG. 3A illustrates an earpiece 111 receiving a component 102 of a hearing device 101, in accordance with some embodiments of the present disclosure. In particular, some embodiments of earpiece 111 may be implemented as some specific embodiments of earpiece 11 schematically shown in FIGS. 1A-1C. Earpiece 111 comprises a curved wall 112 enclosing receiving space 113. Wall 112 is constituted by a core 117 and a sleeve 121. Core 117 comprises an inner surface 119 and an outer surface 118. Outer surface 118 is configured to point toward an area of the ear, when earpiece 111 is inserted into the ear. Inner surface 119 surrounds receiving space 113. Sleeve 121 adjoins core 117 at inner surface 119 and at outer surface 118. Core 117 further comprises a rear face 120 joining outer surface 118 and inner surface 119. Sleeve 121 adjoins core 117 at its rear face 120 at a free end 115 of wall 112. Core 117 is formed from a material comprising a transition temperature, in accordance with core 17 described above. Sleeve 121 is provided with elastic properties, in accordance with sleeve 21 described above. An original shape 122 of sleeve 121 to which sleeve 121 returns due to its elastic properties, when no force is exerted on the sleeve, is illustrated in FIG. 3A.

Earpiece 111 comprises a bore 116 provided as a through hole in wall 112 at a second open end of receiving space 113. A connector 141 is provided inside bore 116. Wall 112 adjoins connector 141 around bore 116. Connector 141 comprises a first end 142 positioned inside receiving space 113. Connector 141 comprises a second end 143 positioned outside earpiece 111, in particular such that second end 143 is spaced from a second end of earpiece 111 at which bore 116 is provided. Connector 141 comprises a side wall 144 extending from first end 142 to second end 143. A recess 145 is formed around a circumference of side wall 144 at an outer surface of side wall 144. Recess 145 is arranged inside bore 116 such that wall 112 adjoins connector 141 inside recess 145. Inner surface 119 of core 117 comprises a circular surface portion 129 facing connector 141, in particular recess 145 of connector 141, inside bore 116. Sleeve 121 adjoins core 117 at circular surface portion 129 such that sleeve 121 is provided between connector 141, in particular recess 145 of connector 141, and circular surface portion 129. Thus, sleeve 121 fully encloses core 117 at outer surface 118, inner surface 119, and the intermediate surface provided by rear face 120. Connector 141 further comprises a flange 147. Flange 147 is formed by a portion of side wall 144 next to the portion of side wall 144 forming recess 145. Flange 147 abuts on recess 145 in a way that flange 147 is arranged at an inner end of bore 116 inside receiving space 113. Flange 147 is configured to receive component 102 of hearing device 101. The component is a sound tube 102. Sound tube 102 is plugged onto flange 147 such that sound tube 102 extends from flange 147 through an opening 114 of receiving space 113 at free end 115 of wall 112 toward an ambient environment of earpiece 111. Side wall 144 of connector comprises an inner surface having a tubular shape in between first end 142 and second end 143 of connector 141. Thus, connector 141 is configured to be acoustically connected to sound tube 102 and to transmit sound waves propagating through sound tube 102 from first end 142 to second end 143 of connector 141 through a tubular cavity surrounded by side wall 144. In some implementations, the outer surface of flange 147 is configured to receive sound tube 102, the outer surface pointing away from the tubular cavity surrounded by side wall 144, in particular such that the component can be plugged and/or screwed onto the outer surface. In some implementations, the inner surface of flange 147 is configured to receive sound tube 102, the inner surface delimiting the tubular cavity surrounded by side wall 144, in particular such that the component can be plugged and/or screwed onto the inner surface.

Figure 3B:
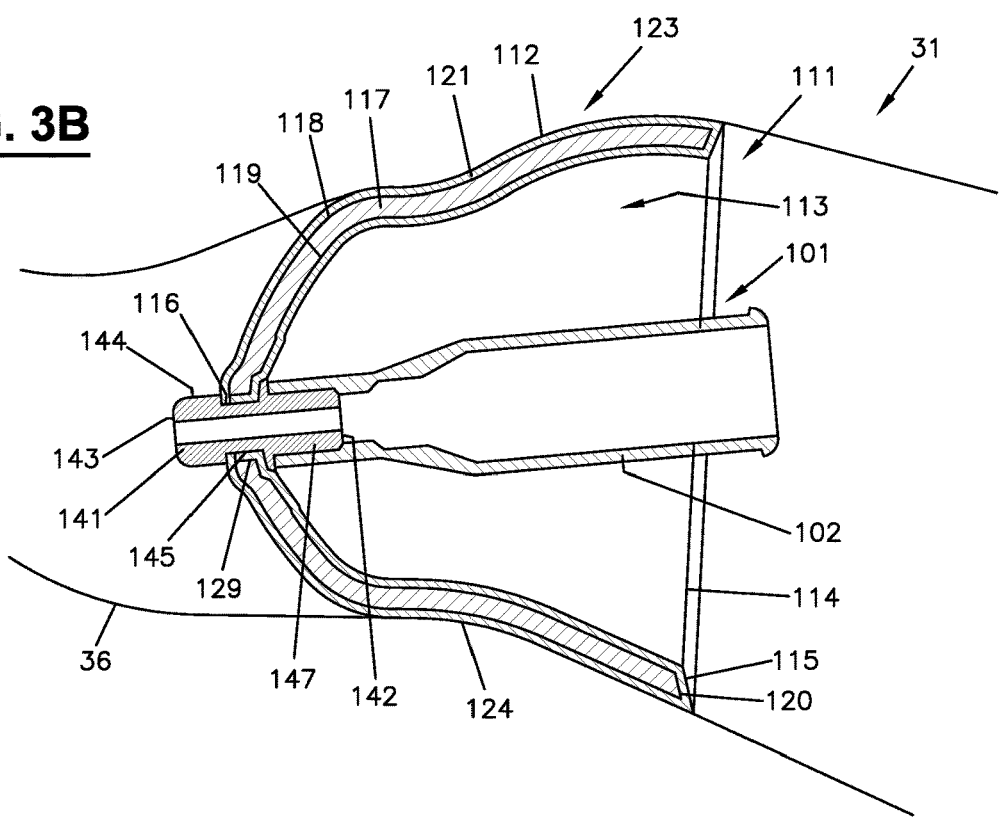
Figure 3C:
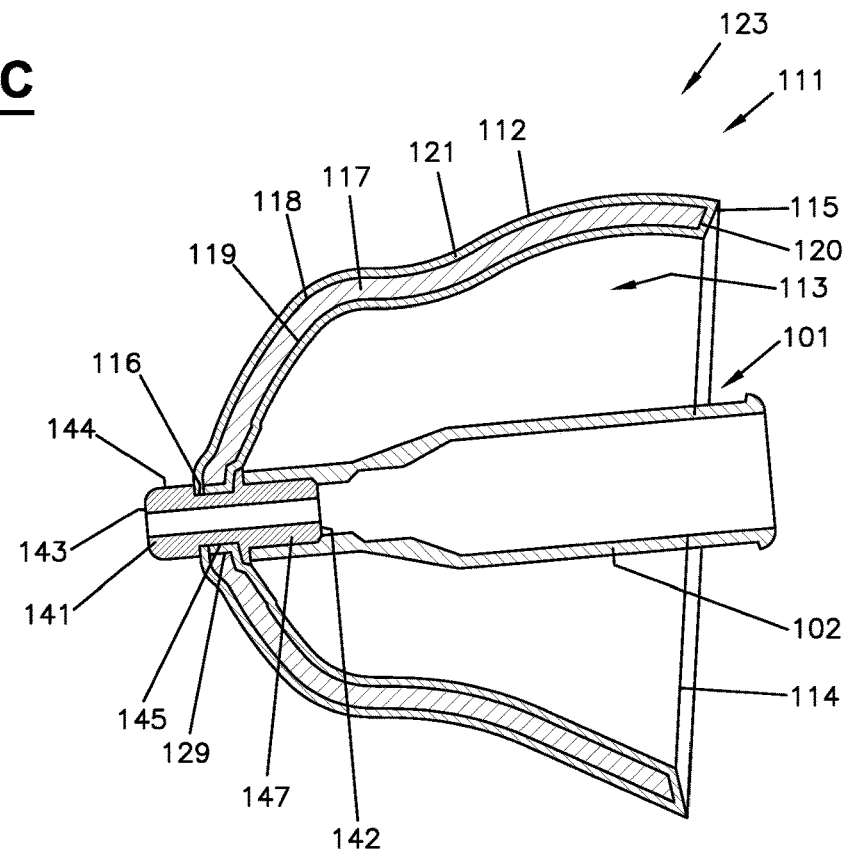

FIG. 3B illustrates earpiece 111 during customization. To this end, core 117 is provided above the transition temperature and earpiece 111 is inserted into ear canal 36 of ear 31. A contact surface 124 is provided by a portion of sleeve 121 adjoining core 117 at its outer surface 118. Contact surface 124 is in contact with ear canal 36 during insertion. By the external forces resulting from the insertion, which are acting on sleeve 121 at contact surface 124, sleeve is deformed from its original shape 222 to a deformed shape 223. Sleeve 121 confines a shaping of core 117 enclosed by sleeve 121, wherein core 117 is provided in its deformable condition, such that core 117 is forced to conform to shape 123 of sleeve 121 above the transition temperature. In this way, earpiece 111 can be customized to the individual shape of ear canal 36. FIG. 3C illustrates earpiece 111 after cooling and removal from ear, wherein deformed shape 23 of sleeve 21 has been conserved in order to provide earpiece 111 customized to the individual ear shape.

Figure 3D:
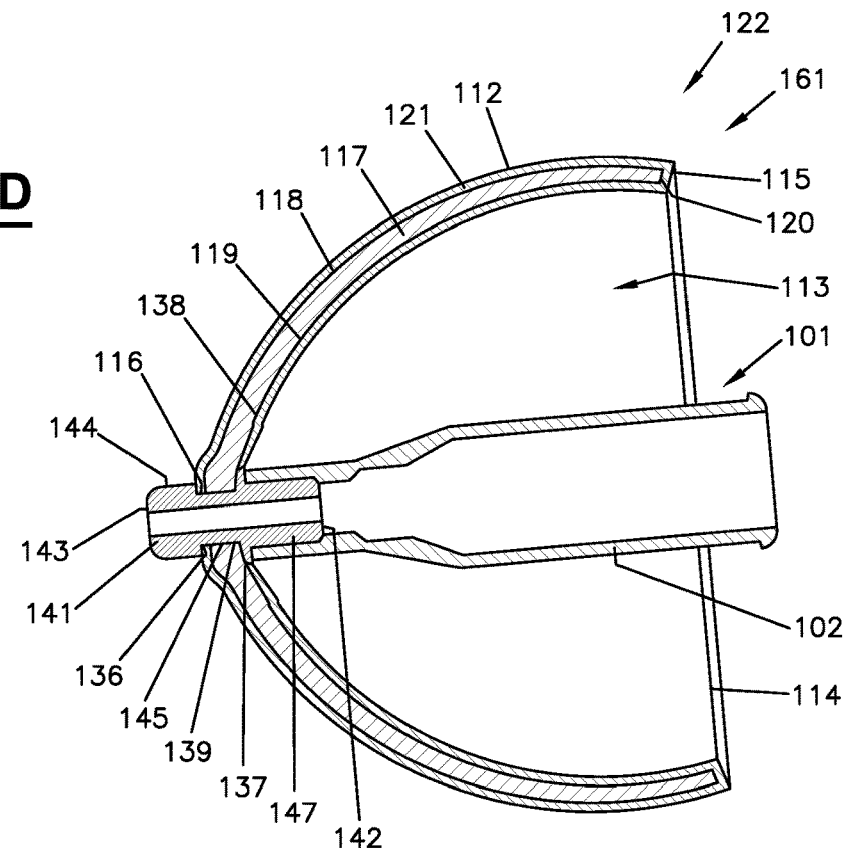
FIG. 3D illustrates a longitudinal-sectional view of an earpiece receiving a component of a hearing device, in accordance with some embodiments of the present disclosure.

FIG. 3D illustrates an earpiece 161 receiving a component 101 of a hearing device in accordance with some embodiments of the present disclosure. Corresponding features with respect to embodiments of earpiece 111 illustrated in FIGS. 3A-3C are illustrated by the same reference numerals. Embodiments of earpiece 161 substantially correspond to embodiments of earpiece 111 illustrated in FIGS. 3A-3C, with the exception that core 117 comprises an inner surface portion 139 at inner surface 119 at which sleeve 121 is not adjoined. Instead, inner surface portion 139 adjoins connector 141, in particular recess 145 of connector 141, inside bore 116. Inner surface portion 139 has a circular shape around its inner circumference with a constant radius of the circle. Sleeve 121 adjoins inner surface 119 of core 117 at a remote inner surface portion 138 neighbouring circular surface portion 139 of core 117 adjoining connector 141. Remote inner surface portion 138 tapers toward circular surface portion 139. A first end edge 136 of the portion of sleeve 121 adjoining outer surface 118 of core 117 adjoins connector 141, in particular recess 145 of connector 141, inside bore 116. A second end edge 137 of the portion of sleeve 121 adjoining surface portion 138 of inner surface 119 of core 117 adjoins connector 141, in particular flange 147 of connector 141. Sleeve 121 encloses core 117 at tapering surface portion 138 of inner surface 119, outer surface 118, and the intermediate surface provided by rear face 120. In this manner, core 117 is bound by sleeve 121, when core 117 is in its deformable condition above the transition temperature. Core 117 conforms to deformed shape 123 of sleeve 121 when sleeve 121 is inserted into ear 31, corresponding to the illustration in FIG. 3B. A customization of earpiece 161 inside ear 31, yielding a deformed shape 123 of sleeve 121 corresponding to the illustration in FIG. 3C after cooling and removal from ear 31, can thus be executed in the same way as described above in the context of FIGS. 3A-C.

FIG. 3E illustrates an earpiece 171 receiving a component 152 of a hearing device 151 in accordance with some embodiments of the present disclosure. Corresponding features with respect to embodiments of earpiece 111 illustrated in FIGS. 3A-3C and embodiments of earpiece 161 illustrated in FIG. 3D are illustrated by the same reference numerals. A connector 181 is provided inside bore 116 at the second open end of receiving space 113. Connector 181 comprises a first end 153 positioned inside receiving space 113. Connector 141 comprises a second end 183 positioned at the second open end of receiving space 113, in particular such that connector 181 substantially sits flush with an outer surface of wall 112 at second end 183. Connector 181 comprises a side wall 185 extending from first end 153 to second end 183. Connector 181 is arranged inside bore 116 such that wall 112 of earpiece 171 adjoins an outer surface of side wall 185. Connector 141 comprises a tubular cavity in between first end 153 and second end 183 surrounded by side wall 185. The tubular cavity is defined by an inner surface of side wall 185. A recess 154 is formed around a circumference of the inner surface of side wall 185. Component 152 of hearing device 151 is provided as a sound tube. Component 152 is plugged into connector 181. In this way, connector 181 is configured to be acoustically connected to component 152 and to transmit sound waves propagating through component 152 from first end 152 to second end 183 of connector 181 through the tubular cavity surrounded by side wall 185. Component 152 comprises a protrusion 155. Protrusion 155 is provided at an outer surface 182 of component 152. Protrusion 155 has a shape substantially matching a shape of recess 154 formed in the inner surface of side wall 185 of connector 181. In this way, sound tube 152 is retained in its position inside connector 181.

FIG. 3F illustrates a perspective section of a core 177, in accordance with some embodiments of the present disclosure. Some embodiments of core 177 may be implemented in some embodiments of earpiece 11 in the place of core 17 illustrated in FIGS. 1A-C and/or in some embodiments of earpiece 111 in the place of core 117 illustrated in FIGS. 3A-C and/or in some embodiments of earpiece 161 in the place of core 117 illustrated in FIG. 3D and/or in some embodiments of earpiece 171 in the place of core 117 illustrated in FIG. 3E. Core 177 is formed from a material comprising a transition temperature, in accordance with core 17, 117 described above. Core 177 comprises an inner surface 179 surrounding a cavity and an outer surface 178 pointing toward an ambient environment. Core 177 comprises intermediate surface 175 joining inner surface 179 and outer surface 178. Inner surface 179 comprises a circular surface portion 172 having a constant radius, a tapering surface portion 174 comprising a taper toward circular surface portion 172, and an axially perpendicular surface portion 173 forming a connecting wall between circular surface portion 172 and tapering surface portion 174. Circular surface portion 172 forms a bore in which a component of a hearing device and/or a connector for a component of a hearing device can be received. Perpendicular surface portion 173 forms a support surface, in particular for the hearing device component and/or a flange of the connector. Inner surface 179 and outer surface 178 are even and/or smooth and/or solid, in particular such that no surface structures are provided on the surfaces. Core 177 substantially has a dome shape. The shape of core 177 illustrated in FIG. 3D may correspond to the shape that core 177 takes in an original shape of a sleeve enclosing core 177, in particular original shape 11 of sleeve 21 and/or original shape 111 of sleeve 121 as depicted in FIGS. 1A-C and/or FIGS. 3A-D.

FIG. 4A illustrates a perspective section of a core 187, in accordance with some embodiments of the present disclosure. Corresponding features with respect to embodiments of core 177 illustrated in FIG. 3E are illustrated by the same reference numerals. Some embodiments of core 187 may be implemented in some embodiments of earpiece 11 in the place of core 17 illustrated in FIGS. 1A-C and/or in some embodiments of earpiece 111 in the place of core 117 illustrated in FIGS. 3A-C and/or in some embodiments of earpiece 161 in the place of core 117 illustrated in FIG. 3D and/or in some embodiments of earpiece 171 in the place of core 117 illustrated in FIG. 3E. Core 187 is formed from a material comprising a transition temperature, in accordance with core 17, 117, 177 described above. Core 187 comprises an inner surface 189 surrounding a cavity and an outer surface 188 pointing toward an ambient environment. Inner surface 189 and outer surface 188 are joined by intermediate surface 175. Inner surface 189 comprises circular surface portion 172, a tapering surface portion 184 comprising a taper toward circular surface portion 172, and perpendicular surface portion 173 in between. Core 187 substantially has a dome shape. The shape of core 187 illustrated in FIG. 4A may correspond to the shape that core 187 takes in an original shape of a sleeve enclosing core 187, in particular original shape 11 of sleeve 21 and/or original shape 111 of sleeve 121 as depicted in FIGS. 1A-C and/or FIGS. 3A-D. A plurality of recesses 186 are formed in outer surface 188 and in tapering surface portion 184 of inner surface 189. Recesses 186 are provided as a through holes extending from outer surface 188 to inner surface 189. Recesses 186 are equidistantly spaced in a circumferential direction of core 187 and/or in an axial direction of core 187. Recesses 186 are circular. Recesses 186 can contribute to a stabilization of core 187 in its deformable condition above the transition temperature, as further detailed below.

FIG. 4B illustrates a longitudinal section of a wall 192, in accordance with some embodiments of the present disclosure. Corresponding features with respect to embodiments of core 187 illustrated in FIG. 4A are illustrated by the same reference numerals. Some embodiments of wall 192 may be implemented in some embodiments of earpiece 11 in the place of wall 12 illustrated in FIGS. 1A-C and/or in some embodiments of earpiece 111 in the place of wall 112 illustrated in FIGS. 3A-C and/or in some embodiments of earpiece 161 in the place of wall 112 illustrated in FIG. 3D and/or in some embodiments of earpiece 171 in the place of wall 112 illustrated in FIG. 3E. Wall 192 comprises core 187, as illustrated in FIG. 4A, and a sleeve 191. Sleeve 191 is provided with elastic properties, in accordance with sleeve 21, 121 described above. Sleeve 191 adjoins core 187 at its outer surface 188 and at its inner surface 189. Sleeve 191 further comprises protrusions 196 extending into recesses 186 of core 187. Protrusions 196 are provided at positions corresponding to positions of recesses 186. Protrusions 196 are provided with a shape corresponding to a shape of recesses 186. Protrusions 196 extend through the total length of the through holes provided by recesses 186. Protrusions 196 connect the portion of sleeve 191 adjoining outer surface 188 of core 187 to the portion of sleeve 191 adjoining inner surface 189 of core 187.

As already mentioned above, recesses 186 of core 187, and corresponding protrusions of sleeve 191, can enhance the stabilization of core 187 in its deformable condition inside sleeve 191. In particular, the bounding of core 187 to a shape of the sleeve 191 above the transition temperature can be further improved by protrusions 196 which can be configured to exert an extra retention force on core 187 inside recesses 186 during a deformation of sleeve 191. Thus, core 187 can be forced to conform to the shape of the sleeve not only at outer surface 188 and inner surface 189 of core 187, but also in between the surfaces 188, 189 along protrusions 196. Beyond that, recesses 186 may also be configured to increase the adhesive forces of core 187 exerted on sleeve 191 below the transition temperature at the junction between recesses 186 and protrusions 196. Thus, an additional stabilization of core 187 above the transition temperature with respect to the shape prescribed by sleeve 191 can be provided and/or an additional adhesion surface in recesses 186 of core 187 can be provided such that the adhesive forces acting on sleeve 191 below the transition temperature can be increased. In this way, the overall stability of wall 192 and the adaptability of core 187 above the transition temperature to a shape prescribed by sleeve 192 may be ameliorated.

FIGS. 5A and 5B illustrate a top view and a lateral view of a wall 212, in accordance with some embodiments of the present disclosure. Internal constituent parts of wall 212 are indicated by dashed lines. Some embodiments of wall 212 may be implemented in some embodiments of earpiece 11 in the place of wall 12 illustrated in FIGS. 1A-C and/or in some embodiments of earpiece 111 in the place of wall 112 illustrated in FIGS. 3A-C and/or in some embodiments of earpiece 161 in the place of wall 112 illustrated in FIG. 3D and/or in some embodiments of earpiece 171 in the place of wall 112 illustrated in FIG. 3E. Wall 212 comprises a core 217 and a sleeve 221. Core 217 is formed from a material comprising a transition temperature, in accordance with core 17, 117, 177, 187 described above. Sleeve 221 is provided with elastic properties, in accordance with sleeve 21, 121, 191 described above. Core 217 comprises an inner surface 219 surrounding a cavity 213 configured as a receiving space for a component of a hearing device. Core 217 comprises an outer surface 218 pointing toward an ambient environment of wall 212. Inner surface 219 and outer surface 218 are joined by an intermediate surface 220 at a rear end of core 217. Sleeve 221 adjoins core 217 at its outer surface 218, at its inner surface 219, and at intermediate surface 220. A free end 215 of wall 212 is provided at the portion of sleeve 221 adjoining intermediate surface 220. Free end 215 encircles a first open end of receiving space 213. A bore 216 is provided as a through hole in wall 212 forming a second open end of receiving space 213. A central axis 210 of receiving space 213 is defined as an axis encompassed by wall 212. Axis 210 runs through the first open end and the second open end of receiving space 213. Wall 212 may have an axial symmetry around axis 210, at least when sleeve 221 is provided in the original shape. Inner surface 219 and outer surface 218 of core 217 taper in the axial direction toward the second open end of receiving space 213.

Recesses 226 are formed in outer surface 218 of core 217. Corresponding protrusions 227 extending into recesses 226 are formed in sleeve 221. Recesses 226 are provided as through holes extending from outer surface 218 to inner surface 219. Protrusions 227 are provided with a shape corresponding to a shape of recesses 226. Protrusions 227 extend through the total length of recesses 226 such that recesses 226 are filled by protrusions 227. In this manner, protrusions 227 connect the portion of sleeve 221 adjoining outer surface 218 of core 217 with the portion of sleeve 221 adjoining inner surface 219 of core 217. Recesses 226 separate core 217 in a plurality of core sections 228. Recesses 226 thus define a respective gap in between core sections 228. Protrusions 227 of sleeve 221 are provided inside recesses 226. Recesses 226 separate core 217 in a direction of axis 210. Core sections 228 thus extend in the axial direction of receiving space 213. Recesses 226 decrease in the axial direction toward the second open end of receiving space 213, in particular with increasing tapering of inner surface 219 of core 217. Correspondingly, a width of protrusions 227 decreases toward the second open end of receiving space 213. Core sections 228 comprise lateral faces 229 provided as intermediate surfaces joining inner surface 219 and outer surface 218 of core 228. Two lateral faces 229 are provided in each core section 228. Lateral faces 229 of each core section 228 are opposing each other. Two lateral faces 229 of neighbouring core sections 228 are facing each other. Recesses 226 are laterally limited by lateral faces 229 of neighbouring core sections 228.

In this way, additional retention surfaces are provided by lateral faces 229 of core sections 228, which can increase the overall stability of wall 212, in particular by providing an additional stabilization of core 217 above the transition temperature with respect to the shape prescribed by sleeve 221 and/or by providing an additional adhesion surface at lateral faces 229 such that the adhesive forces acting on sleeve 221 below the transition temperature can be increased, as already described above in greater detail in the context of embodiments of wall 192 illustrated in FIG. 4B. Moreover, the axial orientation of recesses 226 can bring additional advantages. In particular, lateral faces 229 also extend in the axial direction of receiving space 213. Therefore, a predominant axial stabilization of core 217 can be caused by lateral faces 229 above the transition temperature. Such an additional axial stability of wall 212 may be in particular desirable when an earpiece comprising wall 212 is intended to be inserted into an ear in a direction of axis 210. Supplementary, protrusions 227 of sleeve 221 extending in the axial direction of receiving space 213 can offer yet another advantage of wall 212. Axial protrusions 227 of sleeve 221 allow an increased flexibility of wall 212 in the axial direction due to the elastic properties of the sleeve. Consequently, an increased axial flexibility of an earpiece comprising wall 212 can be achieved, which can improve the insertability of the earpiece into an ear and the wearing comfort of the earpiece after insertion into the ear. This advantage can especially be exploited below the transition temperature of core 217, for instance during daily usage of the earpiece customized to the ear.

Figure 6A:
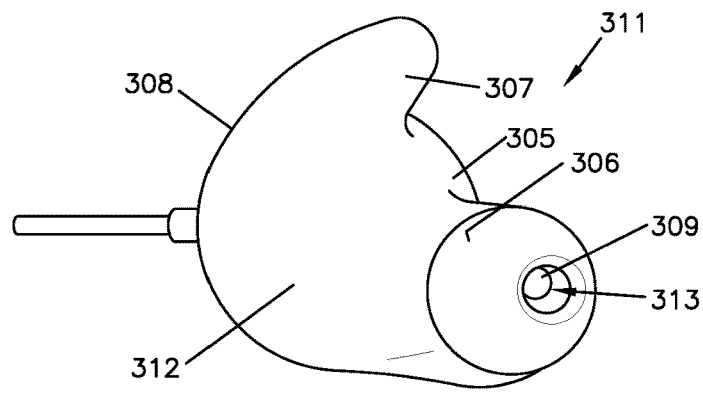
FIGS. 6A, B illustrate an earpiece in a perspective view and in a longitudinal sectional view, in accordance with some embodiments of the present disclosure.

FIG. 6A illustrates an earpiece 311 in a perspective view, in accordance with some embodiments of the present disclosure. Earpiece 311 comprises an outer surface 305. Outer surface 305 is pointing toward an area of the ear, when the earpiece is inserted into the ear. In particular, outer surface 305 comprises a first surface portion 306 configured to be inserted into an ear canal of an ear. Outer surface 305 comprises a second surface portion 307 configured to contact the ear outside the ear canal. Outer surface 305 comprises a third surface portion 308 facing away from the ear when earpiece 311 is partially inserted the ear. A cable 302 of a hearing device is arranged at third surface portion 308. Earpiece 311 comprises an inner surface 309. Inner surface 309 delimits a cavity 313 extending through earpiece 311 from first surface portion 306 to third surface portion 308 of outer surface 305. Cavity 313 may provide a receiving space configured to receive a component of a hearing device, in particular a sound tube of a hearing device. Cavity 313 may be configured to form a sound conduit, in particular a sound tube, allowing a propagation of sound waves from an opening at third surface portion 308 to an opening at first surface portion 306.

Figure 6B:
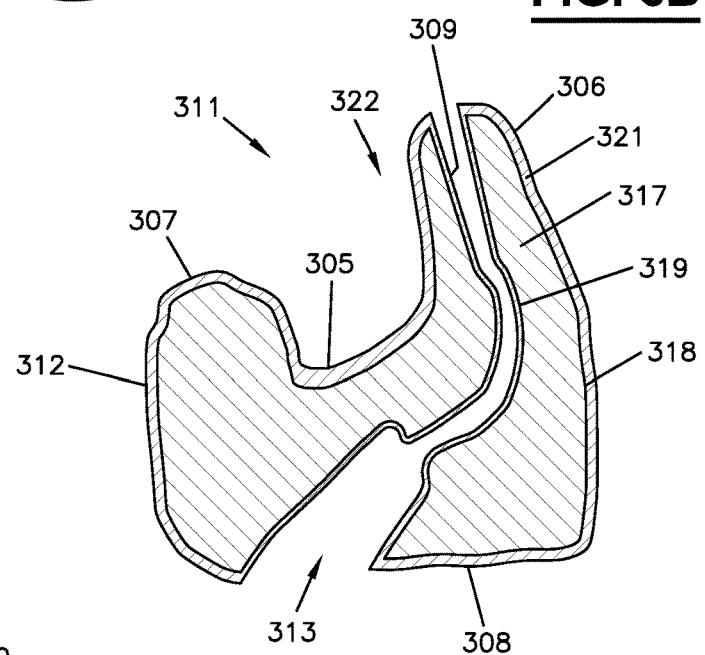
FIG. 6C illustrates an earpiece in a longitudinal sectional view, in accordance with some embodiments of the present disclosure.

FIG. 6B illustrates earpiece 311 in a longitudinal sectional view. Earpiece 311 comprises a preformed body 312 enclosing cavity 313. Body 312 is constituted by a core 317 and a sleeve 321. Core 317 is formed from a material comprising a transition temperature, in accordance with core 17, 117, 177, 187, 217 described above. Sleeve 321 is provided with elastic properties, in accordance with sleeve 21, 121, 191, 221 described above. Core 317 comprises an inner surface 319 and an outer surface 318. Inner surface 319 surrounds cavity 313. Sleeve 321 adjoins core 317 at inner surface 319 and at outer surface 318. Outer surface 318 points away from cavity 313. In this way, outer surface 318 is configured to point toward an area of the ear, when earpiece 311 is inserted into the ear. FIG. 6B depicts earpiece 311 in an original shape 322 of sleeve 321. A customization of earpiece 311 inside an ear, in which sleeve 321 can be provided in a deformed shape, can be executed in the same way as described above in the context of FIGS. 3A-C. This example may illustrate that some embodiments of the present disclosure can be applied to a large variety of earpieces, including earpiece 311 having a rather complex shape. The rather complex shape can be maintained during the customization of the earpiece due to the advantageous elastic properties of the sleeve, which can provide a template for the core to be formed inside the sleeve in its deformable condition.

Figure 6C:
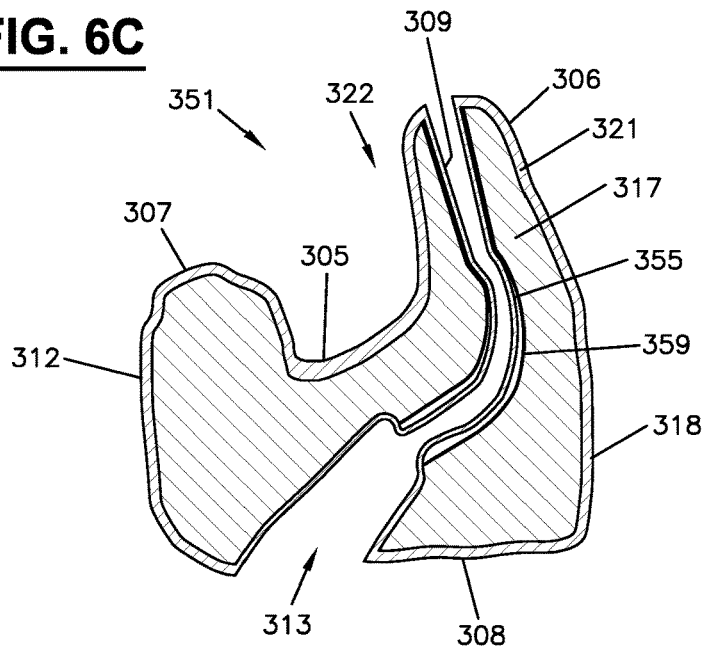

FIG. 6C illustrates an earpiece 351 in a longitudinal sectional view, in accordance with some embodiments of the present disclosure. Corresponding features with respect to embodiments of earpiece 311 illustrated in FIGS. 6A, 6B are illustrated by the same reference numerals. Earpiece 351 substantially corresponds to earpiece 311 with a difference that earpiece 351 further comprises a stiffening member 355. Stiffening member 355 is positioned between an inner surface 359 of core 317 surrounding cavity 313 and a portion of sleeve 321. Sleeve 321 adjoins core 317 at inner surface 359 and at outer surface 318. Only a portion of inner surface 359 of core 317, however, is adjoined to sleeve 321. Another portion of inner surface 359 of core 317 is adjoined to in inner surface of stiffening member 355. Sleeve 321 is correspondingly adjoined to an outer surface of stiffening member 355. Stiffening member 355 is configured to increase the rigidity in earpiece 351 at certain areas of sleeve 321 adjoining stiffening member 355. In some implementations, stiffening member 355 is formed from the same material than sleeve 321. Due to combined thicknesses of stiffening member 355 and sleeve 321 as compared to a thickness of sleeve 321 without stiffening member 355, the rigidity can be increased in this area. In some implementations, stiffening member 355 is formed from a different material than sleeve 321, in particular a material offering an increased rigidity. In such a manner, stiffening member 355 can be configured to bias against forces exerted on earpiece 351 upon insertion of earpiece 351 into the ear. Therefore, stiffening member 355 can advantageously contribute to a conservation of a general shape that shall be maintained during shaping of earpiece 351. A provision of such a stiffening member 355 can be particularly advantageous, when a rather complex shape of earpiece 351 shall be maintained during customization of earpiece 351.

Figure 7:
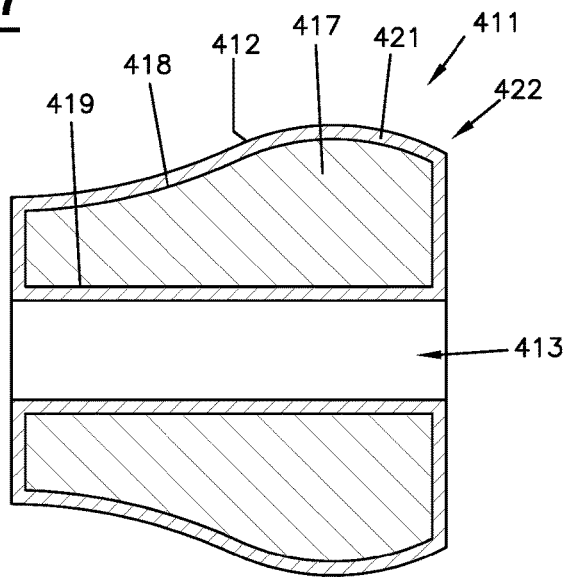
FIG. 7 illustrates an earpiece in a longitudinal sectional view, in accordance with some embodiments of the present disclosure.

FIG. 7 illustrates an earpiece 411 in a longitudinal sectional view, in accordance with some embodiments of the present disclosure. Earpiece 411 comprises a conical body 412. Body 412 is constituted by a core 417 and a sleeve 421. Core 417 is formed from a material comprising a transition temperature, in accordance with core 17, 117, 177, 187, 217, 317 described above. Sleeve 421 is provided with elastic properties, in accordance with sleeve 21, 121, 191, 221, 321 described above. Core 417 comprises an inner surface 419 and an outer surface 418. Inner surface 419 surrounds a cavity 413. Cavity 413 may provide a sound tube and/or may be configured to receive at least one component of a hearing device. Cavity 413 has a circular cylindrical shape. A desired shape of cavity 413 during customization of earpiece 411 may be enforced by providing a stiffening member adjoining sleeve 421 inside cavity 413. For instance, a cylindrical member substantially having an equivalent diameter than cavity 413 may be provided inside cavity 413. Sleeve 421 adjoins core 417 at inner surface 419 and at outer surface 418. Outer surface 418 points away from cavity 413 and is configured to point toward an area of the ear, when earpiece 411 is inserted into the ear. FIG. 7 depicts earpiece 411 in an original shape 422 of sleeve 421. Original shape 422 is conical and may correspond, for instance, to a shape of an in-ear headphone and/or an in-ear headphone adapter. A customization of earpiece 411 inside an ear, in which sleeve 421 can be provided in a deformed shape, can be executed in the same way as described above in the context of FIGS. 3A-C.

Figure 8:
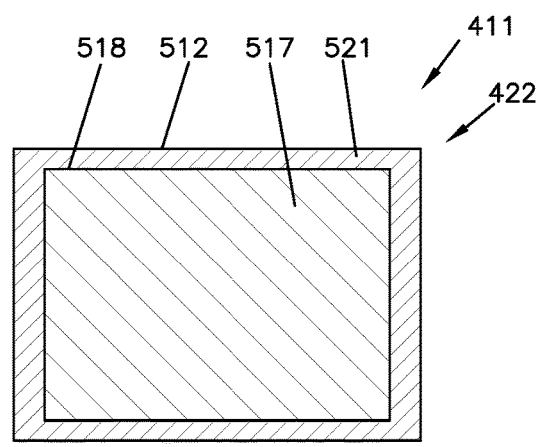
FIG. 8 illustrates an earpiece in a longitudinal sectional view, in accordance with some embodiments of the present disclosure.

FIG. 8 illustrates an earpiece 511 in a longitudinal sectional view, in accordance with some embodiments of the present disclosure. Earpiece 511 comprises a cylindrical body 512. Body 512 is constituted by a core 517 and a sleeve 521. Core 517 is formed from a material comprising a transition temperature, in accordance with core 17, 117, 177, 187, 217, 317, 417 described above. Sleeve 521 is provided with elastic properties, in accordance with sleeve 21, 121, 191, 221, 321, 421 described above. Core 517 is solid and only comprises an outer surface 518. Outer surface 518 is configured to point toward an area of the ear, when earpiece 511 is inserted into the ear. Sleeve 521 adjoins core 517 at outer surface 518. FIG. 8 depicts earpiece 511 in an original shape 522 of sleeve 521. Original shape 522 corresponds to a cylindrical shape, in particular a circular cylindrical shape. Original shape 522 may correspond to a shape of an earplug, in particular a protective ear plug against noise and/or material intrusions, for instance a swim plug offering a protection for an in-ear device against water entering the ear.

A customization of earpiece 511 inside an ear, in which sleeve 521 can be provided in a deformed shape, can be executed in the same way as described above in the context of FIGS. 3A-C.

Figure 9A:
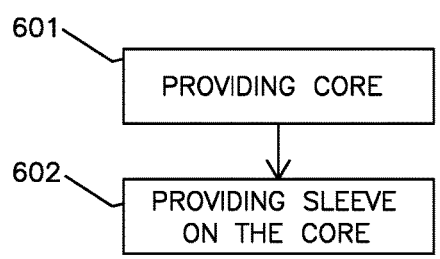
FIGS. 9A, B illustrate a method of manufacturing an earpiece, in accordance with some embodiments of the present disclosure.

FIG. 9A illustrates a method of manufacturing an earpiece, in accordance with some embodiments of the present disclosure. At 601, a core is provided. The material of the core is selected from a material comprising a transition temperature, in accordance with core 17, 117, 177, 187, 217, 317, 417, 517 described above. In some implementations, the core is provided by injection molding. At 602, a sleeve is provided on the core. The sleeve is selected such that the sleeve is provided with elastic properties, in accordance with sleeve 21, 121, 191, 221, 321, 421, 521 described above. In particular, a suitable material and/or shape of the sleeve may be selected to achieve the elastic properties of the sleeve. The sleeve is provided on the core such that the sleeve encloses the core and adjoins the outer surface of the core. In some implementations, the sleeve is molded on the core, in particular by injection molding. In some implementations, the sleeve is provided on the core by dipping and/or spraying the sleeve onto the core.

Figure 9B:
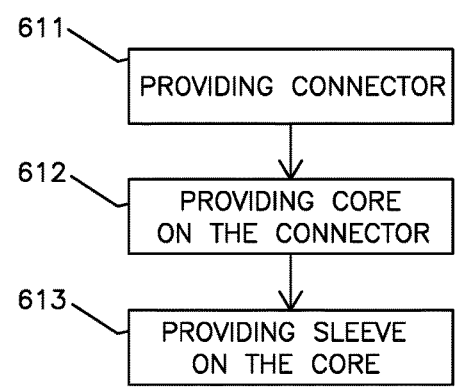

FIG. 9B illustrates a method of manufacturing an earpiece, in accordance with some embodiments of the present disclosure. At 611, a connector is provided. The connector may be configured to allow a propagation of sound waves through the connector. The connector may be configured to receive a component of a hearing device. At 612, a core is provided on the connector. The material of the core is selected from a material comprising a transition temperature, in accordance with core 17, 117, 177, 187, 217, 317, 417, 517 described above. In some implementations, the core is molded on the connector, in particular by injection molding. At 602, a sleeve is provided on the core. The sleeve is selected such that the sleeve has elastic properties, in accordance with sleeve 21, 121, 191, 221, 321, 421, 521 described above. In particular, a suitable material and/or shape of the sleeve may be selected to achieve the elastic properties of the sleeve. The sleeve is provided on the core such that the sleeve encloses the core and adjoins the outer surface of the core. In some implementations, the sleeve is molded on the core, in particular by injection molding. In some implementations, the sleeve is provided on the core by dipping and/or spraying the sleeve onto the core.

While the principles of the disclosure have been described above in connection with specific devices and methods, it is to be clearly understood that this description is made only by way of example and not as limitation on the scope of the invention. The above described preferred embodiments are intended to illustrate the principles of the invention, but not to limit the scope of the invention. Various other embodiments and modifications to those preferred embodiments may be made by those skilled in the art without departing from the scope of the present invention that is solely defined by the claims.

The invention claimed is:

1. An earpiece configured to be at least partially inserted into an ear, the earpiece comprising:
a core comprising a material that during insertion of the earpiece into the ear is deformable above a transition temperature and non-deformable below the transition temperature,
wherein:
a sleeve at least partially encloses the core;
the sleeve has elastic properties selected such that the core conforms to a shape of the sleeve above the transition temperature and the core retains the sleeve in the shape below the transition temperature;
the core has an inner surface surrounding a cavity configured for receiving a component of a hearing device;
the sleeve at least partially encloses the core at the inner surface such that the cavity is delimited by a portion of the sleeve adjoining the core at the inner surface;
the core comprises a plurality of core sections extending in an axial direction of the cavity, two adjacent core sections included in the plurality of core sections having a recess between each other in a circumferential direction of the inner surface surrounding the cavity; and
a protrusion formed in the sleeve is provided inside the recess.

2. The earpiece according to claim 1, wherein the elastic properties are selected such that the sleeve comprises an original shape and that at least above the transition temperature:
the sleeve is deformable from the original shape to a deformed shape during insertion of the earpiece into the ear, and
the sleeve returns to the original shape when no force is exerted on the sleeve.

3. The earpiece according to claim 1, wherein:
the core has an outer surface that faces the sleeve; and
the sleeve at least partially encloses the outer surface of the core such that a portion of an outer surface of the sleeve forms a contact surface for contacting the ear.

4. The earpiece according to claim 1, wherein the sleeve comprises a material selected from a class which includes silicone, an elastomer, polyurethane, and compositions thereof.

5. The earpiece according to claim 1, wherein the cavity forms a bore at an end of the earpiece, the bore configured to be connected to the component of the hearing device.

6. The earpiece according to claim 5, wherein the bore is provided with a connector for the component, the connector configured to connect the earpiece with the component.

7. The earpiece according to claim 1, wherein, the sleeve has a hardness parameter in a range between 20 Shore A and 90 Shore A.

8. The earpiece according to claim 1, wherein the sleeve forms a wall having a thickness in a range of at least 0.1 mm and at most 3.5 mm.

9. The earpiece according to claim 1, wherein the core comprises a thermoplastic polymer.

10. The earpiece according to claim 9, wherein the thermoplastic polymer is selected from a class which includes one or more of polycaprolactone, poly(1,4-butylene adipate), polyethylene, ethylene-vinylacetate-copolymer, or polylactide.

11. The earpiece according to claim 1, wherein an original shape of the sleeve comprises a shape of at least one of an open-ended sleeve, a dome, or a preformed earmold.

12. The earpiece according to claim 1, wherein a stiffening member is provided in the earpiece, the stiffening member adjoining the sleeve and configured to bias against forces exerted on the earpiece upon insertion of the earpiece into the ear.

13. A method of manufacturing the earpiece according to claim 1, the method comprising providing the core, wherein the providing of the core includes providing the sleeve on the core such that the sleeve at least partially encloses the core.

14. The method according to claim 13, wherein the core is provided by injection molding.

15. The method according to claim 14, wherein the core is molded onto a connector of the earpiece.

16. The method according to claim 13, wherein the sleeve is provided on the core by at least one of injection molding, three dimensional printing, compression molding, dipping, manual coating, or spraying the sleeve onto the core.

17. The earpiece according to claim 1, wherein the recess is provided as a through hole from an outer surface to the inner surface of the core.

18. A method of customizing an earpiece to an ear of a user, the earpiece comprising a core comprising a material that during insertion of the earpiece into the ear is deformable above a transition temperature and non-deformable below the transition temperature, wherein a sleeve at least partially encloses the core, and the sleeve has elastic properties selected such that the core conforms to a shape of the sleeve above the transition temperature and the core retains the sleeve in the shape below the transition temperature, the method comprising:

heating the earpiece above the transition temperature of the core such that the core is provided in a deformable condition, inserting the earpiece at least partially into the ear such that the sleeve is contacting the ear and a shape of the sleeve is deformed by the ear, and cooling the earpiece below the transition temperature inside the ear such that the core is provided in a non-deformable condition and the sleeve is retained in the shape by the core.

* * * * *